United States Patent [19]

Marionnet

[11] Plant 4,432

[45] Jul. 10, 1979

[54] STRAWBERRY PLANT

[75] Inventor: Andre Marionnèt, Soings en Sologne, France

[73] Assignee: Jeanne Marionnet-Rabier, Mur de Sologne, France

[21] Appl. No.: 805,246

[22] Filed: Jun. 9, 1977

[51] Int. Cl.[2] ..... A01H 5/08

[52] U.S. Cl. ..... Plt./49

[58] Field of Search ..... Plt./49

[56] References Cited

U.S. PATENT DOCUMENTS

P.P. 3,980 11/1976 Bringhurst et al. ..... Plt./49

P.P. 3,987 12/1976 Johnson ..... Plt./49

*Primary Examiner*—Robert E. Bagwill

*Assistant Examiner*—James R. Feyrer

*Attorney, Agent, or Firm*—Browdy and Neimark

[57] ABSTRACT

A new and distinct variety of strawberry plant is characterized by being an everbearing and very productive variety with the particularity of not producing any stolons. Maintenance of the culture is thus greatly facilitated.

3 Drawing Figures

This invention relates to a distinctly new strawberry variety obtained by natural cross-breeding of seedlings carried out in 1970 at Soings en Sologne in France. Asexual reproduction from the original mother plant was carried out by splitting of the roots and division of the meristem and in vitro micropropagation.

The physiological characteristics are as follows: The seasonal blooming is fairly early, the first blooms appearing under normal conditions in the French climate during the month of April. The season of maturity is fairly early, the first fruit becoming ripe in June. The remontance is continuing, a second blooming starting in June or July until September or October, with the fruit becoming ripe from July to November. Sensitivity to bruises is fairly sensitive. The firmness of the pulp is medium. The taste of the fruit is normal.

The recommended type of culture is plain field.

Figure 1:
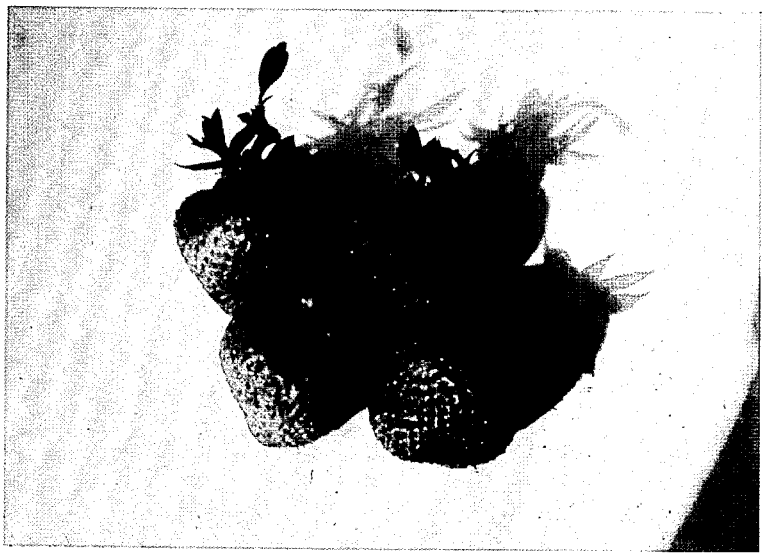
FIG. 1 shows the fruit including the characteristic shape of the fruit.
Figure 2:
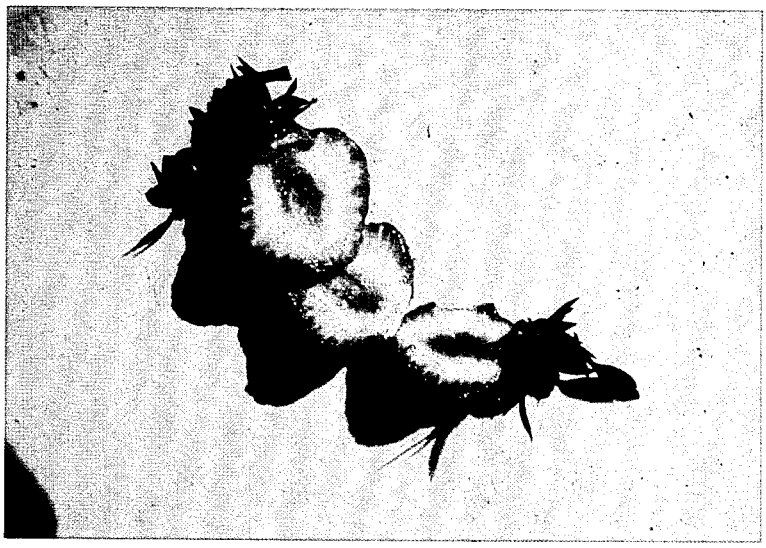
FIG. 2 shows the fruit cut open so as to show a cross-section of the fruit including the nature and color of the pulp.
Figure 3:
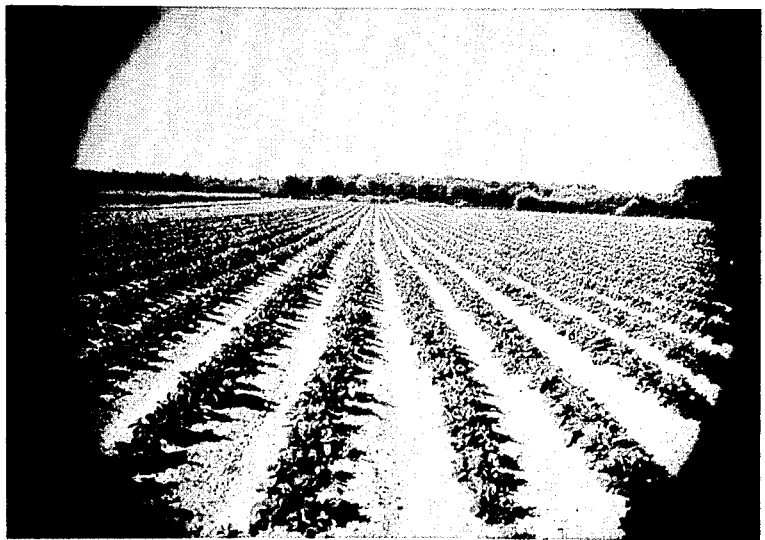
FIG. 3 is a view showing the strawberry plants in cultivation.

The characteristics of the strawberry plant in accordance with the present invention are summarized on the following table:

| MORPHOLOGICAL CHARACTERISTICS | DESCRIPTION |
|---|---|
| GROWTH OF THE PLANT | |
| Habit | More or less spread out |
| Leaf: a) Stem | |
| Angle of Leaf Stem to Main Stem | less than 90° |
| Shape at the Base | V-shaped |
| Pilosity of the Upper Face | Medium |
| Color | Dark Green very near but slightly lighter than that of the variety Tioga |
| Brilliance | Brilliant |
| General Shape (terminal foliage) | Slightly Gutter-Shaped |
| Leaf size | Large |
| Ratio between Length/Width | 1.20 to 1.30 |
| Pilosity of stem | Medium |
| Position of Hair of Stems | Upright |

-continued

| MORPHOLOGICAL CHARACTERISTICS | DESCRIPTION |
|---|---|
| Flowers | |
| No. of Petals: Early Flowers | 5 to 9 |
| No. of Petals: Late Flowers | 5 to 6 |
| Ratio of Length/Width of Petals | More Width than Length |
| Angle between the Petals or double the angle between the Leaf Stem and Petal Postion of Hair on the Peduncle | Obtuse |
| Relative Position of Flowers/Foliage | Laying close to the surface |
| Ratio of Length of Sepalules (s)/Sepals (S) | Under the Foliage |
| Ratio of Length of Sepals (S)/Petals (P) | s < S |
| Stamens | S = P |
| FRUIT | Present |
| Size | Medium |
| Length of Peduncle | Medium |
| Shape of the Early Fruit and the Late Fruit | Similar or identical |
| Shape of the Early Fruit | Biconical |
| Ratio of Width (1)/Height (H) (Early Fruit) | 1 < H |
| Position of the Achenes | Slightly Pushed in |
| Zone of Achenes | Weak |
| Overall External Color | Homogeneous, dark red similar to Tioga variety |
| | The central core is a dark red very close in color to that of wild strawberries; this is surrounded by a whitish pink almost white zone; surrounding the almost white zone and just inside the surface is a medium red zone. |
| Brilliance | Brilliant |
| Postion of the Calyx and the Calicle | Both Upright |
| STOLONS (Well Developed) | |
| Number | Absent |
| PHYSIOLOGIC CHARACTERISTICS | |
| Blooming Season | Fairly Early, e.g. April |
| Maturity Season | Fairly Early, e.g. June |
| Sensitivity to mildew | Little Sensitivity |
| Remontance | Continuous Remontance |
| Sensitivity to Bruises | Medium Sensitivity |
| Firmness of the Pulp | Medium |

What is claimed is:

1. A new and distinct variety of strawberry plant substantially as herein shown and described, characterized by the fact that it is an everbearing and very productive variety with the particularity of not producing any stolons.

* * * * *